(12) United States Patent
Heyes et al.

(10) Patent No.: US 8,535,525 B2
(45) Date of Patent: Sep. 17, 2013

(54) FLUID PROCESSING APPARATUS

(75) Inventors: Keith James Heyes, Barnt Green (GB); Hugh Christopher Bramley, Chipping Norton (GB); Alan Melvyn Bhimani, Birmingham (GB)

(73) Assignee: Quanta Fluid Solutions Ltd., Warwickshire (GB)

( * ) Notice: Subject to any disclaimer, the term of this patent is extended or adjusted under 35 U.S.C. 154(b) by 0 days.

(21) Appl. No.: 13/557,702

(22) Filed: Jul. 25, 2012

(65) Prior Publication Data

US 2013/0037465 A1    Feb. 14, 2013

Related U.S. Application Data

(63) Continuation of application No. 11/919,600, filed as application No. PCT/GB2006/001671 on May 8, 2006, now abandoned.

(30) Foreign Application Priority Data

May 6, 2005   (GB) .................................. 0509330.7
Sep. 7, 2005  (GB) .................................. 0518175.5
Feb. 24, 2006 (GB) .................................. 0603729.5

(51) Int. Cl.
*B01D 35/18*   (2006.01)
*C02F 1/02*    (2006.01)

(52) U.S. Cl.
USPC ......... 210/182; 210/195.2; 210/259; 210/418

(58) Field of Classification Search
None
See application file for complete search history.

(56) References Cited

U.S. PATENT DOCUMENTS

| 3,774,762 | A  |   | 11/1973 | Lichtenstein |
|---|---|---|---|---|
| 5,252,213 | A | * | 10/1993 | Ahmad et al. ................. 210/542 |
| 5,643,201 | A | * | 7/1997 | Peabody et al. ................. 604/31 |
| 2004/0195157 | A1 | * | 10/2004 | Mullins et al. ................. 210/90 |
| 2005/0020961 | A1 |   | 1/2005 | Burbank et al. |
| 2009/0211975 | A1 | * | 8/2009 | Brugger et al. ............... 210/638 |

FOREIGN PATENT DOCUMENTS

DE  100 24 447    11/2001
EP  0 165 751     12/1985

* cited by examiner

*Primary Examiner* — Dirk Bass
(74) *Attorney, Agent, or Firm* — Husch Blackwell LLP (57) ABSTRACT

A machine is provided with a slot to releasably receive and retain a cartridge in which dialysis is effected. The machine is configured for supplying to the cartridge, at a controlled temperature and rate, sterile water for use in haemodialysis and is operable to maintain, in a sterile condition, residual water contained therein after completion of a haemodialysis treatment.

10 Claims, 13 Drawing Sheets

FIG. 14

FLUID PROCESSING APPARATUS

This application is a continuation of application Ser. No. 11/919,600, filed Jan. 26, 2009, which in turn is a national stage application of International Application No. PCT/GB2006/001671 with an International filing date of May 8, 2006.

FIELD OF THE INVENTION

This invention relates to apparatus for the extracorporeal processing of bodily fluids, in particular the extracorporeal dialysis of blood.

BACKGROUND OF THE INVENTION

Most dialysis apparatus currently in use must be very rigorously cleaned between uses to prevent contamination, either cross-contamination from one fluid to another or contamination, with for example bacteria, due to poor sanitation. This is particularly important in haemodialysis, which comprises removing blood from the body, processing it by means of diffusion exchange through a membrane with a dialysis solution, and then returning it to the body. In attempt to reduce the amount of cleaning required, various methods and apparatus have been developed which utilize disposable single-use processing systems.

In these, and in other medical procedures employing disposable fluid processing systems, it is typical for the operator, who may be a trained medical professional, to first select and locate an appropriate filter or membrane element and one or more flow sets. These items must then be removed from their sterile packaging and be connected together to form a fluid circuit, which is then installed on the particular processing apparatus with which the procedure is to be performed. Typically, the processing apparatus includes multiple pump, valve, detection and clamping elements which interact with various parts of the disposable circuit and which are operable to perform the process.

Previous designs to simplify the set up of such processes have proposed that some of the fluid circuit elements be contained in a disposable "cartridge" which can be interfaced with a re-usable machine. Often these systems have been complex requiring either a disposable flexible bag-like circuit to be placed in a non-disposable rigid supporting structure prior to inserting into the machine or requiring tubes to be connected to various elements of a non-disposable component prior to interfacing with the machine. While these designs go some way to providing a solution to the cleaning problem, they are complex and there is scope for error in their use. In haemodialysis in particular, there are two fluid circuits, namely the blood circuit and the processing fluid (i.e. dialysis solution) circuit and while, in the prior proposals, the disposable component includes the full circuit for the blood, the processing fluid is supplied from a re-usable machine. The processing fluid is typically supplied to the cartridge in one of two ways. The first is that large volumes of the sterile process fluid, namely water, containing various additional components, for example sodium bicarbonate, is supplied to the machine. These volumes must be kept under specific conditions and can only be stored for a finite amount of time before bacterial growth begins. In addition, if different patients require the use of different processing fluids this does not provide a universal system. The alternative solution is that the machine is provided with a supply of de-ionised water (commonly in a medical establishment this will be produced centrally and then piped to applications requiring it). The water is then heated in the machine to a temperature at which bacteria are killed and then cooled down to substantially the same temperature as the bodily fluid and then various additives are added to provide the required process fluid. When the machine is dormant between uses with this system it is necessary to sterilize all of the internal fluid lines within the apparatus between uses and consequently, although the system hygiene is improved by the use of disposable parts and the set up is partially simplified for the operator, the down-time between treatments is not reduced because of the cleaning process that is still required. Further, the machine complexity has remained high because of the need to provide the chemical and circulatory fluid paths required for the cleaning process.

OBJECT OF THE INVENTION

Accordingly it is an object of the present invention to provide an improved haemodialysis apparatus wherein the need for cleaning is eliminated or minimised.

SUMMARY OF THE INVENTION

According to the present invention there is provided a machine adapted to releasably receive a cartridge in which dialysis is effected, said machine having means for supplying to the cartridge, at a controlled temperature and rate, sterile water for use in the haemodialysis, the machine being operable to maintain in a sterile condition residual water contained therein after completion of a haemodialysis treatment.

Preferably the machine further comprises a water inlet, for receiving water from a water supply, and a sterile water outlet, for supplying water to a cartridge, wherein said machine is provided with means for sterilising water as it flows from said water inlet to said sterile water outlet.

Preferably the machine is provided with means for recycling the residual water in a closed loop circuit through the means for sterilising said water when the apparatus is not performing haemodialysis of a patient's blood, thus maintaining the residual water in a sterile condition.

In a preferred arrangement the means for sterilising the water comprises means for heating the water to an elevated temperature at which at least micro-organisms and bacteria within the water are destroyed. More preferably the water is heated to at least 85 degrees centigrade. Preferably, subsequent to heating the water to sterilise it, said machine is provided with means to cool the water to substantially body temperature.

In an alternative preferred arrangement the method of sterilisation may be an alternative known technique, for example irradiation techniques may be used.

Preferably the machine further comprises valve means for preventing water from exiting the sterile water outlet when no cartridge is present.

Preferably the machine further comprises two platens, at least one of which is movable in relation to the another, adapted to receive and hold a cartridge in which dialysis is effected therebetween Preferably the platens comprise means that operate on, eg actuate valves and pumps embodied in, the cartridge during haemodialysis.

In a preferred arrangement the sterile water outlet comprises an outlet valve in one of said platens which, when in a first position, presents a flush surface with said platen and prevents water from exiting the sterile outlet and a second position wherein an outlet is formed in the face of the platen allowing the sterile water to pass therethrough. Preferably when the outlet valve is in its first position residual water within the machine is prevented by said outlet valve means from exiting the sterile water outlet, and is circulated around a closed loop within said machine, said closed loop passing the water through the means for sterilising the water, thereby maintaining the residual water in a sterile condition.

Preferably when a cartridge is not present between said platens, the platens sealingly engage against one another such that the water exits said sterile water outlet and is circulated through the platens and through the means for sterilising the water in a closed loop within said machine, thereby maintaining the residual water in a sterile condition.

According to a second aspect of the invention there is provided an apparatus for performing haemodialysis of a patient's blood, the apparatus comprising:

a) a cartridge in which dialysis is effected, the cartridge being connectable by tubing to the patient's blood circulatory system; and b) a machine as described above.

In a preferred arrangement, when the means for sterilising the water comprises means for heating the water to an elevated temperature at which at least micro-organisms and bacteria within the water are destroyed, subsequent to heating the water to sterilise it, the water exits the sterile outlet at an elevated temperature and is cooled to substantially body temperature within the cartridge.

Preferably the cartridge comprises various pumps and valves and the machine comprises two platens, at least one of which is movable in relation to the another, in between which the cartridge is held during use and said platens comprise means of actuating said various pumps and valves.

In a preferred arrangement the sterile water outlet interfaces with the edge of the cartridge.

In a preferred arrangement, when the cartridge in which dialysis is effected is removed from the machine between treatments, a sterilisation cartridge is inserted into the machine through which any residual water in the machine between treatments is circulated as part of the closed loop circuit. Preferably the cartridge has an internal passage way which forms a part of the sterile water loop such that the heated water enters the cartridge via the sterile connector and returns to the apparatus via another connector. More preferably the cleaning cartridge contains a filter element, through which the residual water flows, which removes any particles or contaminants within the closed loop circuit. The cleaning cartridge preferably has means for accepting a cleaning fluid or tablet that can be used to chemically and/or biologically sterilise the closed loop circuit.

Preferably, the cartridge in which dialysis is effected is disposable, being thrown away or recycled after a single use such that a new cartridge is used for each treatment. Preferably all functional elements required for the haemodialysis process that are subject to contamination by blood or waste products or chemicals needed for the process are contained within said cartridge. Thus, by providing a single use disposable dialysis cartridge, firstly the need to clean and sterilise the aforementioned elements is eliminated and secondly there is no danger of cross-contamination from one patient to the next Further, the machine, which preferably includes user-actuable control means for controlling the haemodialysis process carried out in the cartridge, may be re-used successively a number of times without the need to clean it because of its being operable to maintain, in a sterile condition, residual water contained in it after completion of a treatment. Accordingly, cleaning operations on the apparatus may be completely eliminated over an extended period of time, although it may be desirable to clean the water supply elements comprised in the machine, using, for example, chemical cleaning agents, after it has been used a number of times.

In a preferred arrangement the cartridge in which dialysis is effected is provided with at least one connection means for connection with a fluid additive supply whereby an additive, for example bicarbonate or bicarbonate solution, is supplied directly to said cartridge for admixture to the sterile water thereby forming dialysate solution, without contacting any non disposable parts of the apparatus. Alternatively any fluid additives required for the treatment may be contained within the cartridge.

According to a third aspect of the present invention there is provided a cleaning cartridge having a water inlet, a water outlet and a flowpath therebetween, said cartridge being adapted for releasable connection to a machine as described above and forming a part of a closed loop sterilisation circuit of said machine.

Preferably the cleaning cartridge contains a filter element, through which the residual water flows, which removes any particles or contaminants within the closed loop circuit. More preferably the cleaning cartridge has means for accepting a cleaning fluid or tablet that can be used to chemically and/or biologically sterilise the closed loop circuit.

According to a fourth aspect of the invention there is provided a cartridge for releasable connection to a machine so as to provide apparatus as defined above.

A preferred machine and cartridge of the invention comprise, in combination, a number of novel and inventive features as are described below with reference to the accompanying drawings, but it is to be understood that a machine and/or cartridge of the invention may comprise any one or more of those features.

Embodiments of the invention will now be described by way of example only with reference to the following, largely diagrammatic, drawings in which.

BRIEF DESCRIPTION OF THE DRAWINGS

DETAILED DESCRIPTION

Figure 1:
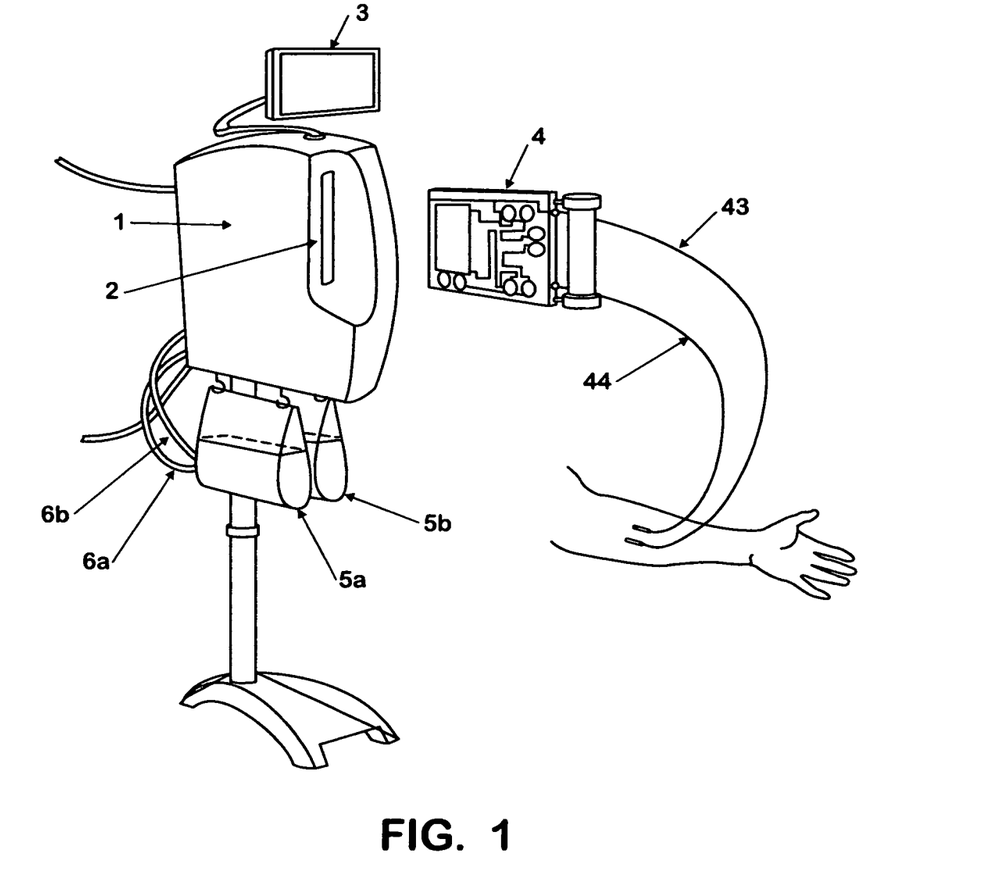
FIG. 1 is a front perspective view of the haemodialysis apparatus showing the reusable machine and disposable cartridge separate from one another.

Referring to FIG. 1, a haemodialysis system is shown which comprises a machine 1 containing a slot 2 adapted to accept and retain therein a cartridge 4, and an operator interface 3. The combination of machine and cartridge together, when connected to a patients circulatory system, perform an extracorporeal haemodialysis process on the patients blood before returning it to the patient. The operator interface 3 both permits control of the dialysis functions, and provides status and warning information as required.

Figure 2:
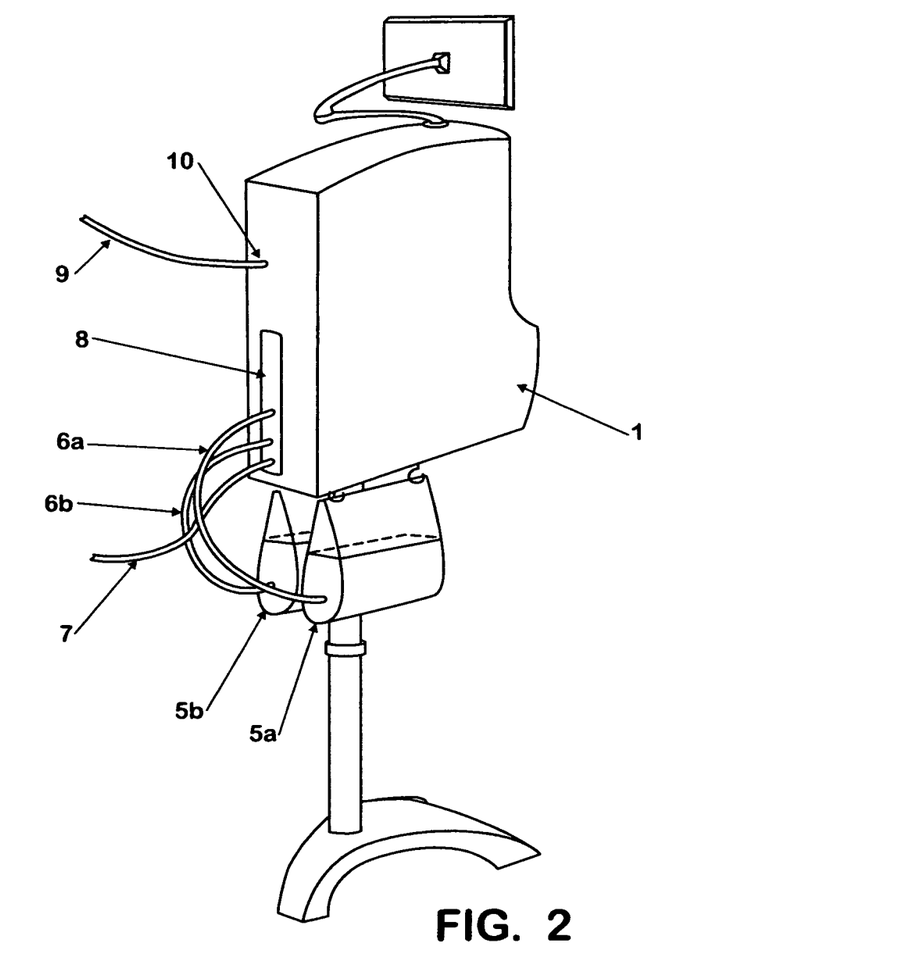
FIG. 2 is a rear perspective view of the machine shown in FIG. 1.

Referring to FIGS. 1 and 2 when the cartridge 4 is inserted into the slot 2 of the machine 1, an aperture 8 at the rear of the machine provides access to couple a drain tube 7 and one or more supplementary supply tubes 6a, 6b directly to the rear of the cartridge 4. The tubes 6a, 6b draw supplementary additives from containers 5a, 5b which are shown mounted under the machine 1. An external deionised water supply pipe 9 connects directly to the machine through water inlet 10. Arterial and Venous blood tubes 43,44 already attached to the cartridge 4 permit connection of the dialysis system to the patient's blood system.

Figure 3:
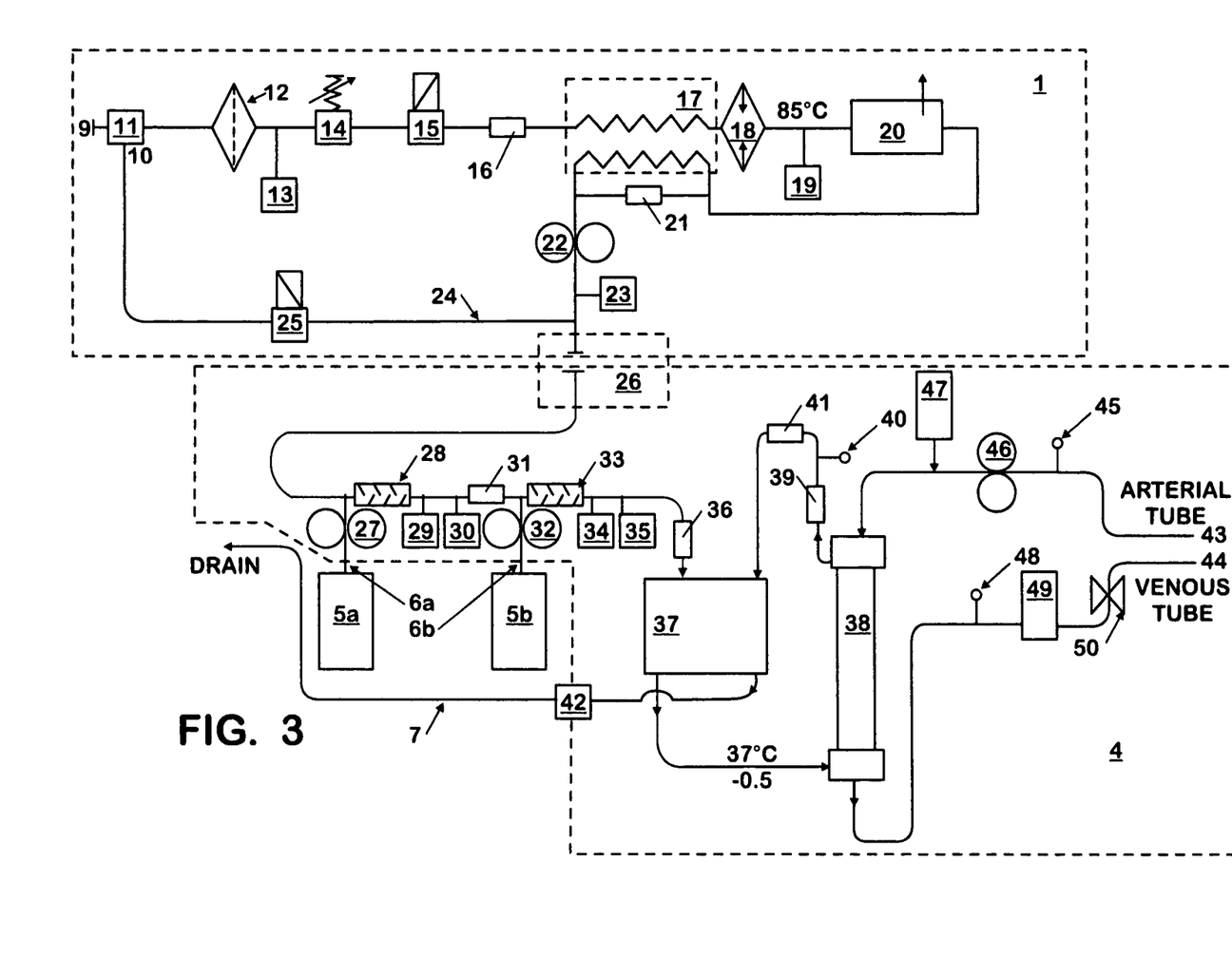
FIG. 3 is a schematic flow diagram of the haemodialysis process carried out by the apparatus of FIG. 1.

FIG. 3 shows a fluid flow schematic diagram of the dialysis system, the general nature of which will be familiar to those skilled in the art of haemodialysis. The fluid circuit components 10 to 25 incorporated in the machine part of the system are only exposed to the de-ionised water supply, and do not suffer any contamination from the dialysis process. De-ionised water enters the machine at water inlet 10 incorporating a non-return valve 11 and flows through filter 12, pressure regulator 14, and on/off solenoid 15. A low pressure switch 13 stops the process if water supply pressure falls below a preset minimum acceptable level. A master flow sensor 16 forms part of the water flow control system. The water is preheated in heat exchanger 17, and heated to eighty five degrees centigrade by heater 18, controlled by sensor 19. Heating the water to this temperature is sufficient to destroy any bacteria and or micro-organisms in the water. After passing through the de-aeration system 20, the water is cooled in heat exchanger 17, before passing to pump 22. To avoid the need for a supplementary heater in the cartridge, a by-pass valve 21 is adjusted by the control system to provide an output temperature, as sensed by temperature sensor 23, of approximately 37° C. from the machine to the cartridge 4. If there is a temperature drop of the process fluid within the cartridge before the process fluid enters the dialysis filter 38 then the temperature of the water exiting the machine may be higher than 37 degrees centigrade so that, taking the temperature drop into consideration, the water is at 37 degrees centigrade when it enters the dialysis filter 38. The water leaves the machine 1 at sterile water outlet 26 and enters the cartridge 4. The sterile outlet 26 is designed to close off, or be closed off, when the cartridge 4 is decoupled from the machine 1. When there is no cartridge 4 present, recirculation control valve 25 is opened, and water flows through the recirculation loop 24, and no new water enters the system. As a result the temperature of the whole water loop rises to at least about 85° C., maintaining the sterility of the machine 1 water system. Connectors 10 and 26 are designed such that water flushes all the contact areas to eliminate any bacterial growth Referring again to FIG. 3, the cartridge 4 comprises two separate fluid paths, one for the dialysis fluid, and one for the patient's blood. Water enters the cartridge from the machine at connector 26 and is mixed with a predetermined amount of supplementary additive, e.g. bicarbonate, in mixer 28. The supplementary additive is supplied from container 5a by pump 27. Correct ratio of supplementary additive is determined by controlling pump 27, but is also checked by temperature 29 and conductivity 30 measurements. A secondary flow sensor 31 may be used to confirm the flow rate of the mixture. Similarly, a second supplementary additive, e.g. acetate, can be added in precise amounts from container 5b through pump 32, mixer 33, temperature sensor 34, conductivity sensor 35, and tertiary flow sensor 36. The fluid mixture passes through a balancing and ultrafiltration system 37, before entering the dialyser 38. The waste fluid from the dialyser passes through flow measurement station 39, pressure sensor 40 and blood leak detection unit 41, before entering the balancing unit 37, after which it passes via connector 42 on the cartridge 4 direct to drain line 7.

The extracorporeal circuit will be familiar to those skilled in the art of haemodialysis, and is shown set up for twin needle dialysis. Blood from the patient enters the cartridge via arterial tube 43 and its pressure is measured by sensor 45 before it enters the circulation pump 46. Anti clotting agent such as Heparin is then added by dosing unit 47, prior to the dialyser 38. The cleansed blood leaving the dialyser again has a pressure measurement 48, before entering an air detector section 49. The blood is then returned to the patient via a venous clamp 50, and the venous tube 44.

It will be appreciated that at the end of the treatment, extracting the cartridge 4 from the machine 1 removes all contaminated flow passages and components, leaving the machine 1 in a clean and sterile condition, a condition that may be maintained by recirculating and heating residual water in the machine 1 as described earlier. The need for subsequently cleaning and sterilising the machine after each treatment is thereby eliminated, although it may be desirable from time to time to carry them out.

Figure 4:
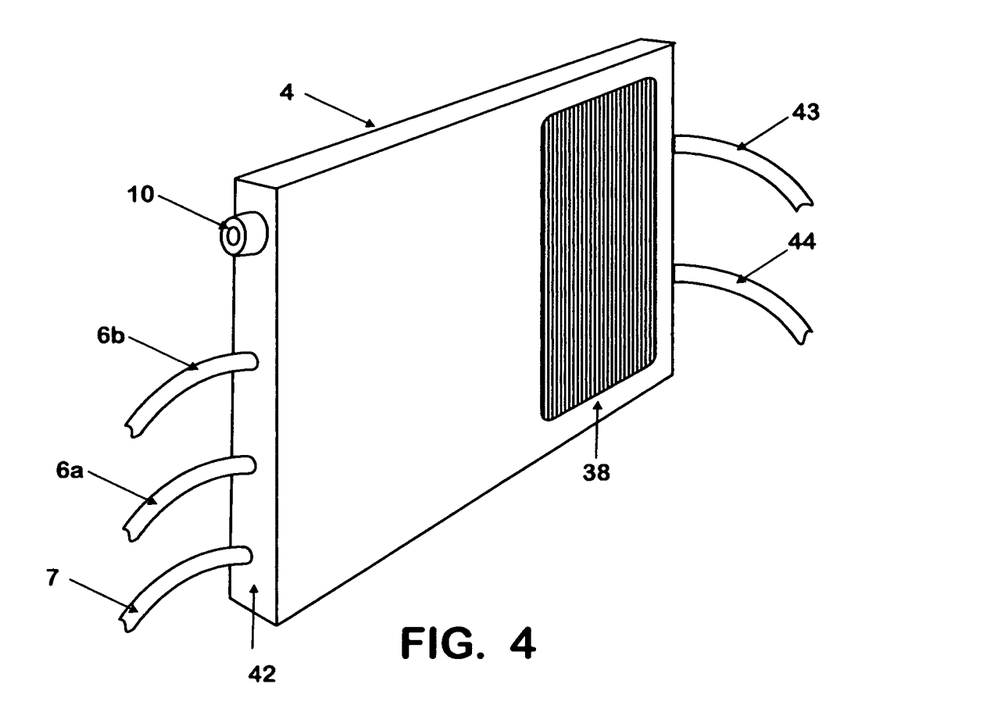
FIG. 4 is a perspective view of one embodiment of a cartridge with an internal dialysis filter.

Turning now to the cartridge, FIG. 4 is a view of one embodiment of the cartridge 4 in which the dialyser 38 filter elements are incorporated within the cartridge. Water connector 10 engages with the water supply line (not shown) within the machine on insertion, and connector 42 for the drain 7 and the supplementary additive supply tubes 6a/b, are accessed directly at the rear of the cartridge. The cartridge is provided with Arterial 43 and Venous 44 tubes for connection to the patient's circulatory system.

Figure 5:
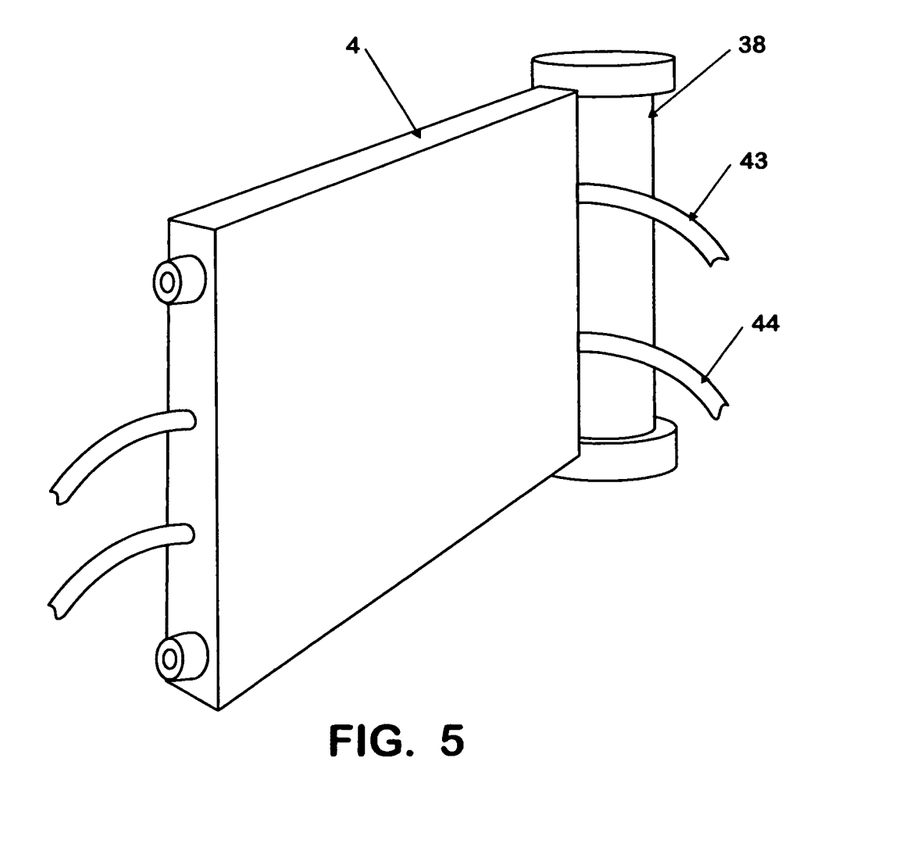
FIG. 5 is a perspective view of an alternative cartridge having an external dialysis filter.

FIG. 5 is a view of an alternative embodiment of the cartridge 4 in which the dialyser 38 is separate from the cartridge, and is of a proprietary commonly available design. In this embodiment, the dialyser is supplied separately, and is attached to the cartridge 4 at a sterile location, immediately prior to inserting the cartridge in the machine 1.

Figure 6:
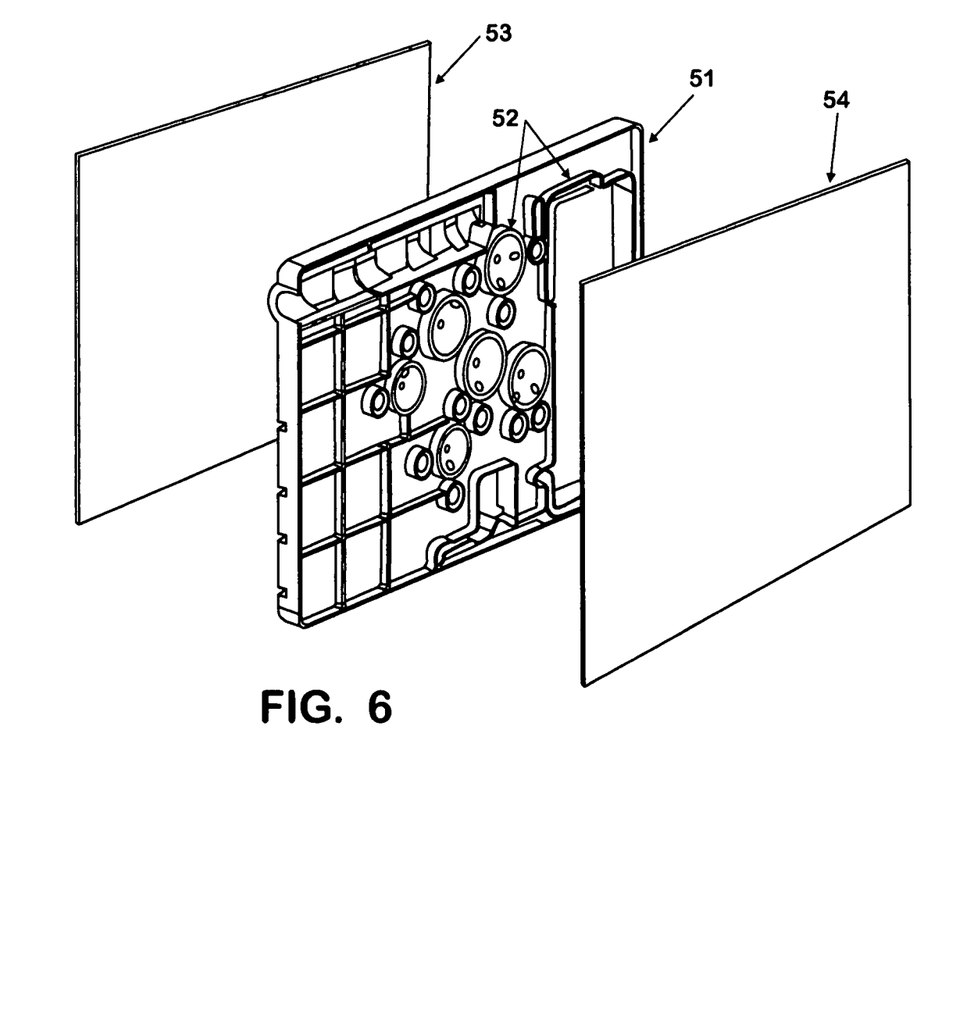
FIG. 6 is an exploded perspective view of a cartridge.

The basic construction of the cartridge is illustrated, as an exploded perspective view, in FIG. 6. A central planar core 51, which is preferably a plastic moulding, has upstanding walls 52 which define flow passages and cavities for the pumping, valving and sensing elements of the process. Flexible films 53, 54 cover the front and rear faces of the core 51, and are sealably attached to at least the perimeter of the core 51.

Figure 7:
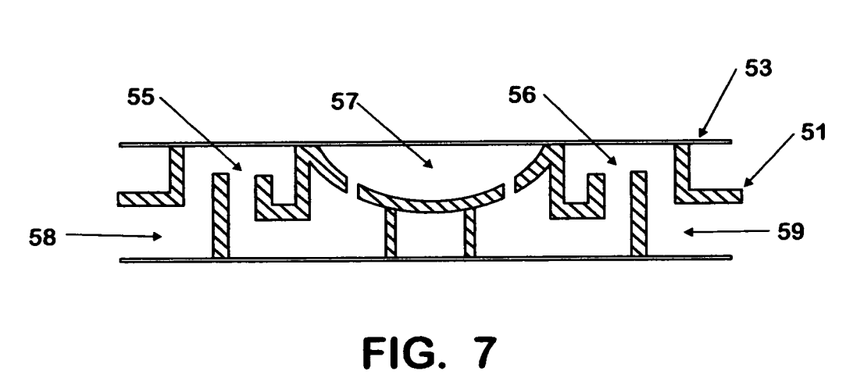
FIG. 7 is a cross-sectional view of a typical cartridge pumping element.

A key feature of the design of the cartridge 4 shown in FIG. 6 is the interface between the machine 1 and the cartridge 4 whereby the actuating means for operating the valving and pumping elements, and the transmitters and receivers for sensing are all contained in the machine "side of the interface, and operate on the elements within the cartridge by way of the flexible films FIG. 7 illustrates the operation of a typical cartridge pumping element. Valve elements 55 and 56 are formed in the cartridge core 51, together with pumping chamber 57. These are all covered by film 53. Actuating means situated in the machine cooperate with these elements to displace the film to perform valve and pumping actions. In the embodiment shown, fluid at high and low pressure is admitted sequentially to the film areas above elements 55, 56 and 57. By opening and closing the inlet valve 55, and the outlet valve 56 while displacing the film 53 over pumping chamber 57 in an appropriate sequence, fluid in the cartridge is displaced from entry flow passage 58 to exit passage 59.

Figure 8A:
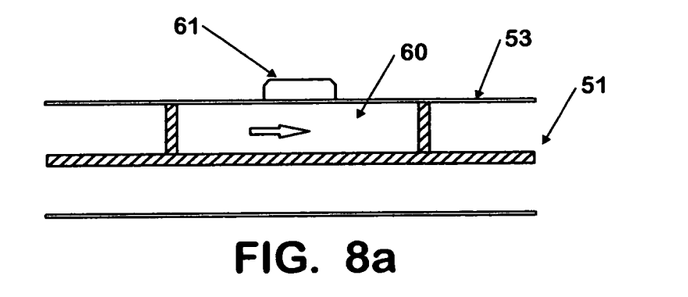
FIGS. 8 and 8a are cross sectional views of a typical pressure measurement element of a cartridge.
Figure 8B:
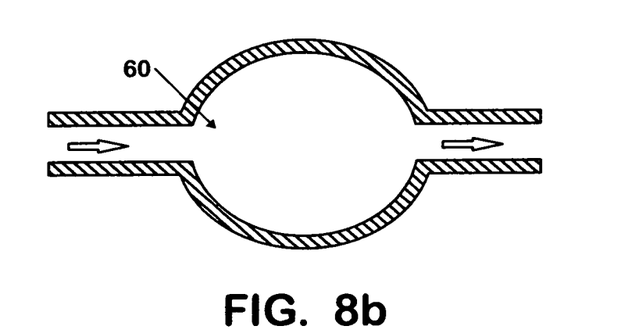

FIGS. 8 and 8a illustrate a pressure measuring element. A chamber 60 is formed in the core 51 in a flow passage. The film 53 covering this chamber acts as a diaphragm, and is acted upon by the pressure of the fluid in the passage. A force transducer 61 mounted within the machine measures the force on the diaphragm, from which the pressure can be calculated.

Figure 9:
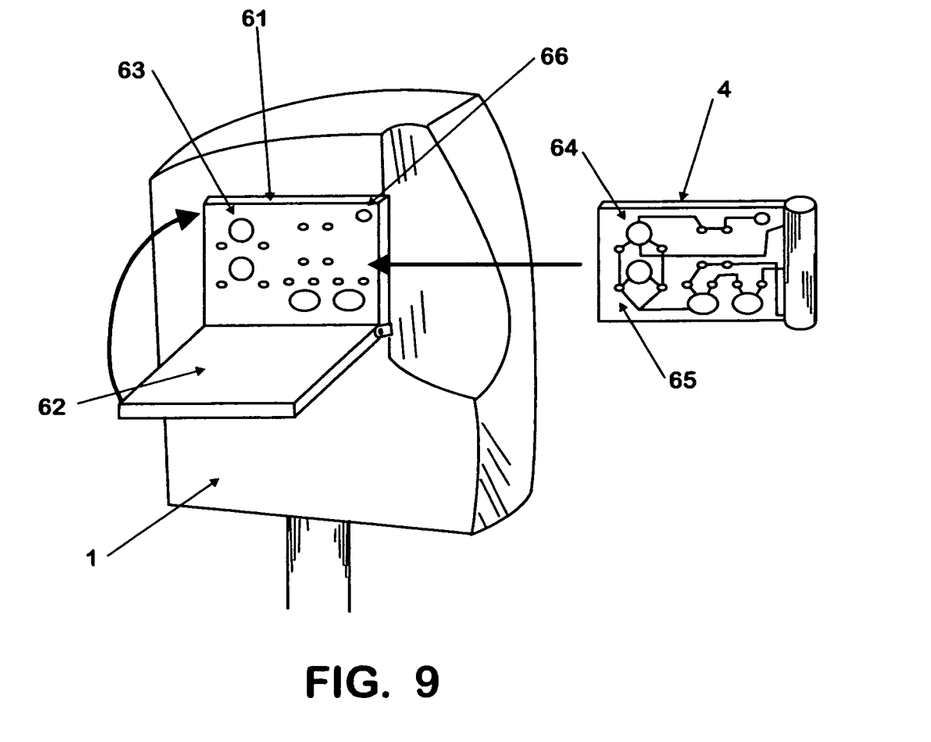
FIG. 9 is a perspective view of a close-up of part of the machine showing the platens.
Figure 10:
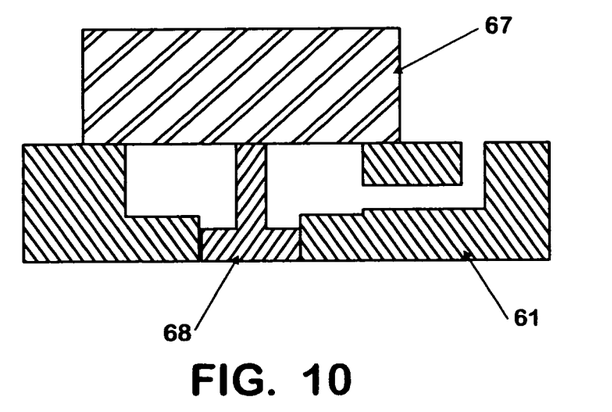
FIGS. 10, 11 and 12 are cross-sectionional views of a sterile water outlet incorporating a flush valve.
Figure 11:
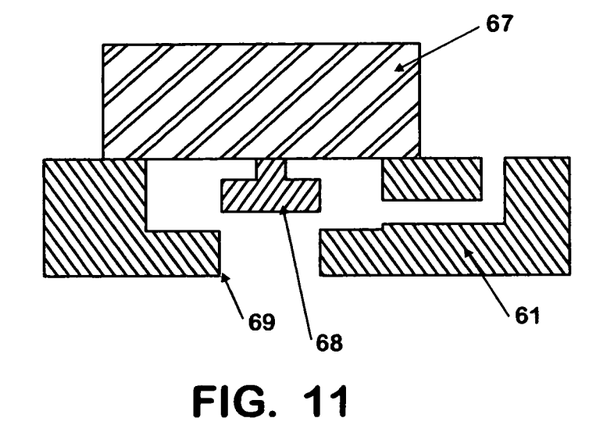
Figure 12:
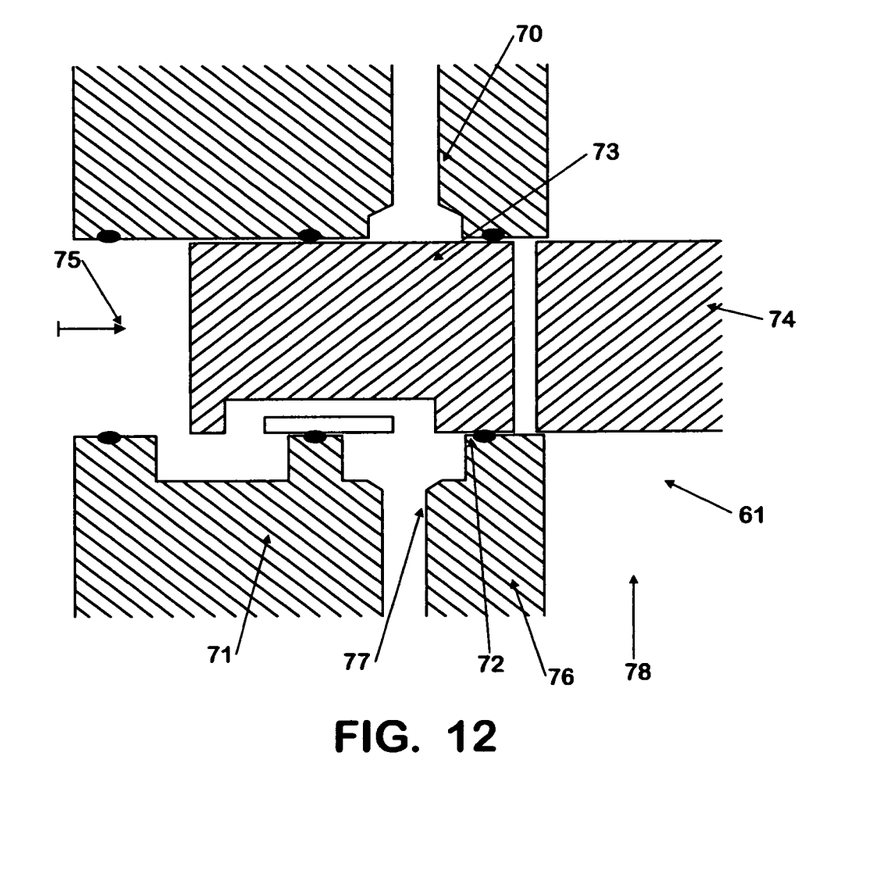

Referring to FIG. 9 the apparatus is shown with a fixed platen 61 and a movable platen 62 between which the cartridge is inserted and held. In operation the cartridge 4 is placed in position and the movable platen 62 is pivoted into place. It is then clamped to hold the cartridge 4 in sealing contact with the fixed platen 61. The clamping is performed by actuator means (not shown) which are attached to the fixed platen. Alternatively of course simple mechanical clamping means could be used. The fixed platen 61 has provided in its surface a number of depressions 63 which align with pumps 64 and valves 65 on the cartridge 4 to control the flow of fluid therethrough. The machine 1 has pressure and vacuum pumps (not shown) and associated valving to provide a supply of pressure or vacuum to the various depressions 66. The pressure and vacuum causes the flexible membrane (53, FIG. 6) of the cartridge 4 to be displaced to open or close valves or to pump fluid through the fluid circuit of the cartridge 4. The fluid circuit of the cartridge 4 is as described herein, in particular as described in reference to FIG. 3. A sterile water outlet 65 from the machine is provided in the fixed platen 61 through which sterile water from the machine 1 passes to enter the cartridge 4. Referring now also to FIGS. 10 to 12 details of the sterile connector are shown. The connector is situated in the fixed platen 61 and comprises an actuator 67 and a plunger 68. The plunger 68 is located in a bore 69 in the platen 61 such that when the connector 66 is in its closed position in which there is no fluid flow through the connector 66 to a cartridge 4, the plunger 68 sits such that it is flush with the surface of the platen 61. Being flush the platen 61 can easily be swabbed before treatment commences with cleaning fluids, for example antibacterial agents. The bore 69 and the plunger 68 are both provided with a slight taper such that a good sealing face is achieved between them. The connector 66 may form a seal by using precision sized parts or alternatively an O-ring or other compliant seal material may be presented in the bore to prevent any fluid passing between the bore and the plunger 68. FIG. 10 shows a connector 66 in a closed position, i.e. the position the connector would assume when a cartridge 4 is not in place and no fluid flow therethrough is required and FIG. 11 shows a connector 66 in an open position whereby fluid may pass through it. The cartridge has a compliant seal means surrounding the point of entry of sterile water such that when presented to the sterile connector 66 and clamped in place a seal is made between the cartridge 4 and the platen 61 surrounding the connector 66 preventing leakage of the sterile water.

Referring now to FIG. 12, a connector 66 is shown that additionally the functionality of the recirculation control valve (25 FIG. 3) to enable the sterile water to be circulated through a closed loop when the connector 66 is in its closed position. The connector comprises a plunger 70 slideable in a bore 71, in the platen 61, said plunger 70 having two internal passageways 72, 73. The plunger 70 is movable between a first position in which water can flow from an inlet passage 74. through passageway 72 and out through the connector 66 to a cartridge 4 and a second position, in which the water flowing through the inlet passageway 74 passes through the plunger and exits through an outlet passageway 75 to recirculate through the sterilising means (not shown). 0-rings 76 are provided to prevent passage of water between the plunger 70 and the platen 61. When the plunger 70 is in its second position its end face 77 is flush with the surface 78 of the platen 61. When used this connector negates the necessity of separate valve 25 in the circuit diagram shown in FIG. 3.

Figure 13:
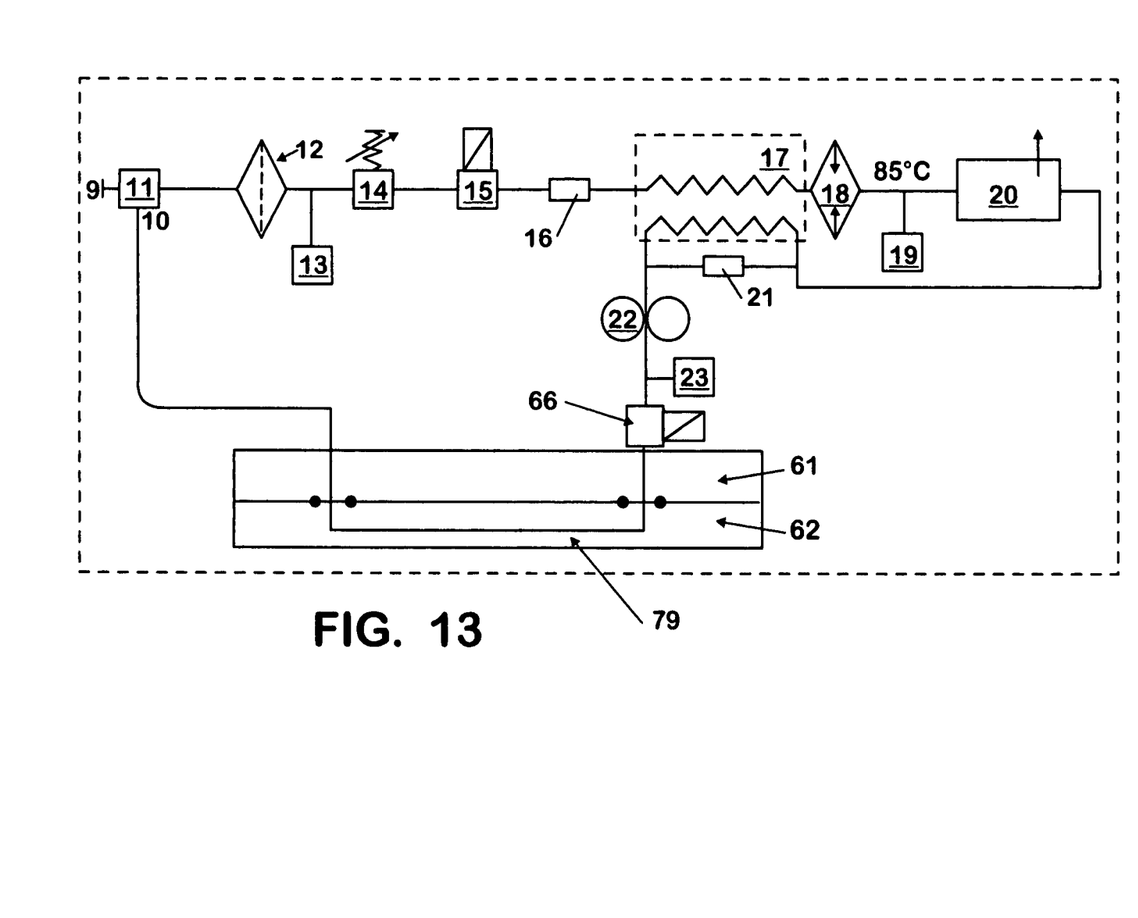
FIG. 13 is a schematic diagram of an apparatus in accordance with the invention having a closed loop water circuit passing through the platens.

Referring to FIG. 13 a schematic diagram of the machine is shown. The majority of the fluid circuit for the machine is the same as described in reference to FIG. 3. A sterile connector 66 is provided at the fixed platen 61. The connector is of the sort as described above with reference to FIGS. 10 and 11. When there is no cartridge between the platens 61, 62 the movable platen 62 moves into position adjacent to platen 61 and is clamped thereto making sealing contact therewith. Platen 62 has an internal flowpath therethrough which allows water to flow through the connector 66 through the flowpath 79, back into platen 61 and rejoin the sterilisation circuit of the machine. In this manner, when not being used to perform dialysis, i.e. when there is no cartridge present, the water may be recirculated through a closed loop circuit within the machine allowing the temperature to raise to approximately 85 degrees centigrade thereby maintaining the water in a sterile condition.

Figure 14:
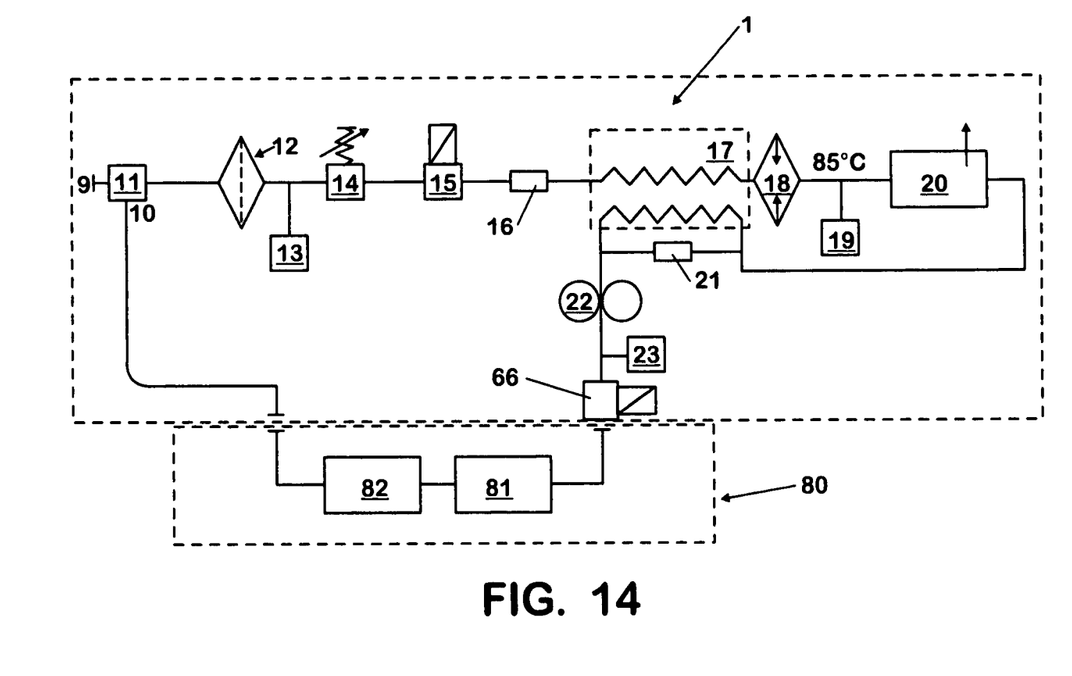
FIG. 14 is a schematic diagram of an apparatus in accordance with the invention including a cleaning cartridge.

Referring to FIG. 14 a schematic diagram of an apparatus is shown comprising the machine 1 and a cleaning cartridge 80. The flowpath of the machine is identical to that described in reference to FIG. 13 but instead of circulating the water through the movable platen to maintain it in a sterile condition when there is no cartridge in place, the cleaning cartridge 80 is positioned between the platens and clamped into place such that water circulates thorough the cleaning cartridge 80 and back into the machine 1, rejoining the sterilisation circuit of the machine 1. Within the cleaning cartridge 80 there is a filter 81 to remove any solid or particulate matter that may get in the circuit when changing from dialysis to cleaning cartridge, and cleaning chemicals 82 to chemically clean the inside of the water circuit.

The invention claimed is:

1. A machine adapted to releasably receive a cartridge in which dialysis is effected, said machine comprising:
    a fluid circuit for supplying to the cartridge, at a controlled temperature and rate, sterile water for use in the hemodialysis, the machine being operable to maintain in a sterile condition residual water contained therein after completion of a hemodialysis treatment, wherein said fluid circuit recycles residual water contained therein after completion of a hemodialysis treatment in a closed loop circuit through a sterilizer when the machine is not performing hemodialysis of a patient's blood, thus maintaining the residual water in a sterile condition;
    a water inlet for receiving water from a water supply;
    a sterile water outlet for supplying water to the cartridge, wherein said sterilizer sterilizes water as it flows from said water inlet to said sterile water outlet; and
    two platens, at least one of which is movable in relation to the other, adapted to receive and hold the cartridge, and
    wherein the sterile water outlet comprises an outlet valve in one of said platens which, when in a first position, presents a flush surface with said one platen and prevents water from exiting the sterile outlet and, when in a second position, an outlet is formed in the face of said one platen allowing the sterile water to pass therethrough into the cartridge.

2. A machine according to claim 1, wherein the sterilizer comprises a heater for heating the water to an elevated temperature at which at least micro-organisms and bacteria within the water are destroyed.

3. A machine according to claim 2, wherein said machine is provided with a heat exchanger to cool the water, prior to its supply to the cartridge, to substantially human body temperature.

4. A machine adapted to releasably receive a cartridge in which dialysis is effected, said machine comprising:
  a fluid circuit for supplying to the cartridge, at a controlled temperature and rate, sterile water for use in the hemodialysis, the machine being operable to maintain in a sterile condition residual water contained therein after completion of a hemodialysis treatment, wherein said fluid circuit recycles residual water contained therein after completion of a hemodialysis treatment in a closed loop circuit through a sterilizer when the machine is not performing hemodialysis of a patient's blood, thus maintaining the residual water in a sterile condition;
  a water inlet for receiving water from a water supply;
  a sterile water outlet for supplying water to the cartridge, wherein said sterilizer sterilizes water as it flows from said water inlet to said sterile water outlet; and
  two platens, at least one of which is movable in relation to the other, adapted to receive and hold the cartridge, and
  wherein the sterile water outlet is located in one of the platens and, when a cartridge is not between said platens, the platens sealingly engage against one another such that the water exits said sterile water outlet and is circulated through the platens and through the sterilizer in said closed loop within said machine, thereby maintaining the residual water in a sterile condition.

5. An apparatus for performing hemodialysis of a patient's blood, the apparatus comprising:
  a) a cartridge in which dialysis is effected, the cartridge being connectable by tubing to the patient's blood circulatory system;
  b) a machine, to which the cartridge is releasably connectable, for supplying to the cartridge, at a controlled temperature and rate, sterile water for use in the hemodialysis, the machine being operable to maintain in a sterile condition residual water contained therein after completion of a hemodialysis treatment;
  wherein the machine has a water inlet for receiving water from a water supply, and a sterile water outlet for attachment to the cartridge;
  wherein said machine is provided with a sterilizer for sterilizing water as it flows from said water inlet to said sterile water outlet;
  wherein the machine comprises two platens, at least one of which is movable in relation to the other, in between which the cartridge is held during use, and
  wherein the sterile water outlet comprises an outlet valve which, when said outlet valve is in a closed position, presents a flush surface with one of said platens and prevents water from exiting the sterile outlet and, when said outlet valve is in an open position, an outlet is formed in the face of said one platen allowing the sterile water to pass therethrough into the cartridge.

6. The apparatus according to claim 5, wherein the sterilizer comprises a heater for heating the water to an elevated temperature at which at least micro-organisms and bacteria within the water are killed.

7. An apparatus according to claim 6, wherein, subsequent to heating the water to sterilize it, said apparatus is provided with a heat exchanger to cool the water to substantially human body temperature.

8. An apparatus for performing hemodialysis of a patient's blood, the apparatus comprising:
  a) a cartridge in which dialysis is effected, the cartridge being connectable by tubing to the patient's blood circulatory system;
  b) a machine, to which the cartridge is releasably connectable, for supplying to the cartridge, at a controlled temperature and rate, sterile water for use in the hemodialysis, the machine being operable to maintain in a sterile condition residual water contained therein after completion of a hemodialysis treatment;
  wherein the machine has a water inlet for receiving water from a water supply, and a sterile water outlet for attachment to the cartridge;
  wherein said machine is provided with a sterilizer for sterilizing water as it flows from said water inlet to said sterile water outlet;
  wherein said apparatus recycles residual water contained therein after completion of a hemodialysis treatment in a closed loop circuit through the sterilizer when the apparatus is not performing hemodialysis of a patient's blood, thus maintaining the residual water in a sterile condition;
  wherein the machine comprises two platens, at least one of which is movable in relation to the other, in between which the cartridge is held during use, and
  wherein the sterile water outlet is located in one of the platens and, when the cartridge is not connected to said machine, the platens sealingly engage against one another such that the water exits said sterile water outlet and is circulated through the platens and through the sterilizer in a closed loop within said machine, thereby maintaining the residual water in a sterile condition.

9. An apparatus according to claim 8, wherein the cartridge in which dialysis is effected is disposable and is provided with at least one connector for connection to a fluid additive supply whereby an additive is supplied directly to said cartridge for admixture to the sterile water thereby forming dialysate solution, said dialysate solution contacting only the disposable cartridge of the apparatus.

10. An apparatus according to claim 8 to wherein the cartridge in which dialysis is effected has contained within said cartridge, fluid additives for admixture to the sterile water to form dialysate solution.

* * * * *